United States Patent [19]

Hestermann et al.

[11] 4,189,449
[45] Feb. 19, 1980

[54] PRODUCTION OF QUATERNARY PHOSPHONIUM HYDROXIDES

[75] Inventors: Klaus Hestermann, Erftstadt Bliesheim; Hartfried Vollmer, Erftstadt Liblar, both of Fed. Rep. of Germany

[73] Assignee: Hoechst Aktiengesellschaft, Fed. Rep. of Germany

[21] Appl. No.: 924,709

[22] Filed: Jul. 14, 1978

[30] Foreign Application Priority Data

Jul. 20, 1977 [DE] Fed. Rep. of Germany ....... 2732751

[51] Int. Cl.$^2$ .............................................. C07F 9/54
[52] U.S. Cl. ............................................ 260/606.5 F
[58] Field of Search ................................. 260/606.5 F

[56] References Cited

U.S. PATENT DOCUMENTS

| | | | |
|---|---|---|---|
| 3,251,883 | 5/1966 | Rauhut et al. | 260/606.5 F |
| 3,452,098 | 6/1969 | Vullo | 260/606.5 F |
| 3,770,831 | 11/1973 | Maier | 260/606.5 F |

OTHER PUBLICATIONS

Kosolapoff et al., Organic Phosphorus Compounds, Wiley Intersc., N.Y., vol. 2, p. 194 (1972).
Chemical Abstracts, 42 519g (1948).
Kosolapoff, Organophosphorus Compounds, John Wiley & Sons Inc., N.Y., p. 14 (1950).

*Primary Examiner*—Helen M. S. Sneed
*Attorney, Agent, or Firm*—Connolly and Hutz

[57] ABSTRACT

Quaternary phosphonium hydroxides of the general formula:

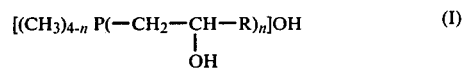

(I)

in which R stands either for hydrogen or an aliphatic or aromatic hydrocarbon having 1 to 12 carbon atoms and n stands for 1 or 2, are made by reacting a di- or trimethylphosphine in an aqueous medium with an epoxide of the general formula

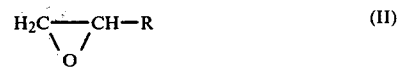 (II)

in which R has the meaning given above. More specifically a pH-value of $\geq 12$ is established in the aqueous medium by means of a base and the starting materials are mixed in said medium.

6 Claims, No Drawings

PRODUCTION OF QUATERNARY PHOSPHONIUM HYDROXIDES

The present invention relates to a process for making quaternary phosphonium hydroxides of the general formula $$[(CH_3)_{4-n}P(-CH_2-CH(OH)-R)_n]OH \quad (I)$$

in which R stands either for hydrogen or an aliphatic or aromatic hydrocarbon having 1 to 12 carbon atoms, preferably 1 to 6 carbon atoms, and n stands for 1 or 2, which comprises reacting in an aqueous medium, a di- or trimethylphosphine with an epoxide of the general formula:

$$H_2C\underset{O}{\overset{\diagdown\;\diagup}{-}}CH-R \quad (II)$$

in which R has the meaning given above.

It is known that betaines or phosphonium hydroxides are obtained in the absence of an acid by reacting an epoxide with a phosphine in an aqueous or anhydrous medium. (G. M. Kosolapoff, L. Maier, Organic Phosphorus Compounds, Wiley-Intercience, vol. 2, 194 (1972)). This known reaction is effected at a pH-value of approximately 7.

A disadvantage encountered with this known process resides in the fact that the reaction proceeds initially very reluctantly and then very vigorously. In this exothermal reaction, the reaction mixture is rapidly warmed up so that portions of readily volatile di- or trimethylphosphine are liable to be expelled from the reactor, and withdrawn from the reaction with the epoxide.

In accordance with our present invention, we now provide an improved process for making quaternary phosphonium hydroxides, which comprises: establishing a pH-value of $\geq 12$ in the aqueous medium with the aid of a base and mixing the starting components together in said medium. The aqueous medium comprises water, which may be used alone or in admixture with an organic solvent. The reaction should preferably be effected at temperatures within the range $-10°$ to $+35°$ C. It is also advantageous to use 1 to 10 mols, preferably 3 to 5 mols, of water per mol of di- or trimethylphosphine, and to use the epoxide in excess over the methylphosphine, based on the stoichiometric quantity necessary to ensure the formation of the particular phosphonium hydroxide to be produced. It is also good practice to establish the desired pH-value in the aqueous medium by means of an alkali metal hydroxide.

It is generally good practice to effect the process of the present invention as follows: The reaction medium, which is either water or a mixture of water with a water-soluble organic solvent, e.g. an alcohol, or with a water-insoluble solvent, e.g. an ether, is placed in a reactor provided with an agitator, thermometer, pH-meter, gas inlet, reflux cooler with gas outlet, and dropping funnel. The reactor should preferably be fed with at least one mol of water per mol of dimethylphosphine or trimethylphosphine. Next, a pH-value equal to, or higher than, 12 is established in the water by means of a base, preferably NaOH.

After this has been done, the quantity of dimethylphosphine or trimethylphosphine to undergo reaction is stirred into the aqueous medium with the resultant formation of a suspension, solution or emulsion depending on whether the aqueous medium is water, a water/alcohol-mixture or a water/water-insoluble ether-mixture. In this latter case, the phosphine is dissolved in the ether and forms an emulsion with the water. Next, the whole is admixed with the epoxide. Depending on its state of aggregation, the epoxide is introduced either through the gas inlet or the dropping funnel. The whole is thoroughly mixed at temperatures of $-10°$ to $+35°$ C. for as long as necessary to ensure the formation of the quaternary phosphonium hydroxide. This is indicated by an increase of the pH to a value higher than 14.

It is naturally possible to add more epoxide than corresponds to the stoichiometric quantity which is necessary to ensure the formation of desirable phosphonium hydroxide. In this event, however, the epoxide in excess may be liable to undergo further reaction under the conditions described to give a polyglycol which is difficult to separate from desirable phosphonium hydroxide. It is therefore advantageous to react 1 mol of alkylphosphine with 1 or 2 mols of epoxide. It is also advantageous to use an excess of alkylphosphine which can readily be separated after the reaction at temperature lower than 40° C., and re-used. The solvent can be separated from the resulting quaternary phosphonium hydroxide by customary distillation under mild conditions, e.g. under vacuum. The quaternary phosphonium hydroxides are obtained in the form of oily, highly hygroscopic and colorless liquids.

It is a special advantage of the present process that by neutralizing the phosphonium hydroxide with a suitable acid, it is possible to produce quaternary phosphonium salts with practically any desirable anion.

The present process which is naturally not limited to the general embodiments described herein, is the first to permit the production, under mild conditions, of methyl-2-hydroxyalkyl(aralkyl)-phosphonium hydroxides which find widespread uses in the form of their salts as flame-retardant agents, vulcanization accelerators, phase transfer catalysts, plant protecting agents, pharmaceutical preparations, and the like.

EXAMPLE 1: [(CH$_3$)$_3$(PCH$_2$—CH$_2$OH]OH 2.5 mols (45 g.) of water heated to 15° C. was placed in a flask which was provided with an agitator, thermometer, pH-meter, gas inlet, reflux cooler with gas outlet, and dropping funnel, and 0.5 mol (38 g.) of (CH$_3$)$_3$P was suspended therein. After the (CH$_3$)$_3$P had been added, the whole was admixed, with vigorous agitation, with 0.5 mol (22 g.) of ethylene oxide. Only after the addition of about 25% of the 0.5 mol of ethylene oxide was the reaction initiated. This was accompanied by strong evolution of heat which was difficult to control and resulted in the partial loss of readily volatile (CH$_3$)$_3$P. The reaction was terminated while a temperature of 15° C. was maintained. The resulting phosphonium hydroxide solution was neutralized by means of a HCl-solution and evaporated to dryness at 110° C. under 20 mm. Hg. The product was taken up (dissolved) in 150 ml. of ethanol and trimethyl-2-hydroxyethyl phosphonium chloride was separated from the solution in the form of colorless crystals with the aid of 1000 ml of acetone. Altogether 55 g. chloride (for identification see Example 2) was obtained. This corresponded to a yield of 70.6% based on (CH$_3$)$_3$P.

To avoid the delay in the start of the reaction, which was noted in Example 1 and which entailed loss of $(CH_3)_3P$, use was made in the following Examples of a reaction medium which had a pH-value of 12 from the onset of the reaction.

EXAMPLE 2: $[(CH_3)_3PCH_2—CH_2OH]OH$ 5 mols. (90 g) of water, which had a pH-value of 12 and was heated to 15° C., was placed in a flask provided with an agitator, thermometer, pH-meter, gas inlet, reflux cooler with gas outlet, and dropping funnel, and 1 mol (76 g) of $(CH_3)_3P$ was suspended therein. After the $(CH_3)_3P$ had been added, the whole was admixed, with thorough agitation, with 1 mol (44 g) of gaseous ethylene oxide. A temperature of 15° C. was maintained by cooling. There was no delay in the start of the reaction during which the initially turbid $(CH_3)_3P$-suspension in water disappeared to give a clear solution of $[(CH_3)_3PCH_2—CH_2OH]OH$ in $H_2O$ which had a pH-value higher than 14. This solution was accurately halved and the two halves were processed separately. One half was concentrated at 30° C. under a vacuum of 0.1 mm Hg to give a colorless, oily, extremely hygroscopic mass. (It was obtained in a yield of 80 g; theoretical yield=69 g.). It was quaternary trimethyl-2-hydroxyethyl phosphonium hydroxide which was contaminated with $H_2O$ and NaOH. The compound was identified in the form of its chloride by NMR-spectroscopy ($^1$H and $^{31}$P-resonances). The values were determined on aqueous solutions (OH-group corresponds to that of $H_2O$). The H-values are based on tetramethylsilane (=O ppm) and the P-shift is based on $H_3PO_4$ of 85% strength.

| P—CH$_3$ : 1.94 ppm | P : −26 ppm |
|---|---|
| P—CH$_2$ : 2.52 ppm | |
| CH$_2$O : 4.00 ppm | |

The second half of the initial reaction product was neutralized by means of an aqueous solution of HCl. The solvent ($H_2O$) was evaporated at 110° C. under 20 mm. Hg and the resulting crystalline solid matter was treated with 150 ml. of ethanol. The phosphonium salt underwent dissolution and was separated from undissolved NaCl. The alcoholic solution was admixed with 1000 ml of acetone and trimethyl-2-hydroxyethyl-phosphonium chloride $[(CH_3)_3PCH_2—CH_2OH]Cl$ was separated therefrom in the form of colorless crystals. 70 g of chloride, corresponding to a yield of 89.7%, was obtained.

The compound had a melting point of 267° C. The following data were determined by elementary analysis:

| | Calculated | Found |
|---|---|---|
| C | 38.6 | 38.8 |
| H | 9.1 | 9.0 |
| P | 19.9 | 19.6 |
| Cl | 22.1 | 22.1 |

EXAMPLE 3: $[(CH_3)_3PCH_2—CH_2OH]OH$

The reaction of Example 1 was repeated but a mixture of 5 mols of $H_2O$ and 5 mols of isopropanol, was used as the reaction medium and the reaction temperature was 30° C. The resulting phosphonium hydroxide solution was neutralized by means of hydrochloric acid and worked up, in the manner described in Example 1, to give $[(CH_3)_3PCH_2—CH_2OH]Cl$. 137 g of final product, corresponding to a yield of 87.5%, was obtained.

EXAMPLE 4: $[(CH_3)_3PCH_2—CH_2OH]OH$

The reaction of Example 1 was repeated but a suspension of 10 mols of $H_2O$ and 3 mols of diethylether was used as the reaction medium and the reaction temperature was 0° C. The resulting aqueous phosphonium hydroxide solution was separated from the ether, neutralized by means of hydrochloric acid and worked up, in the manner described in Example 1, to give $[(CH_3)_3PCH_2—CH_2OH]Cl$. 121 g of final product, corresponding to a yield of 77.3%, was obtained.

EXAMPLE 5: $[(CH_3)_3PCH_2—CHOH-CH_3]OH$ 1 mol (76 g) of $(CH_3)_3P$ was reacted with 1 mol (58 g) of propylene oxide at −10° C. in a mixture of 5 mols of $H_2O$ and 5 mols of isopropanol, which was placed in the apparatus described in Example 1. The resulting phosphonium hydroxide solution was neutralized by means of hydrochloric acid and worked up, in the manner described in Example 1, to give $[(CH_3)_3PCH_2—CHOH—CH_3]Cl$. 154 g of final product, corresponding to a yield of 90.8%, was obtained. The compound was identified by NMR-spectroscopy.

| CH$_3$ : 1.37 ppm | P : −25 ppm |
|---|---|
| PCH$_3$ : 1.92 ppm | |
| PCH$_2$ : 2.44 ppm | |
| CH : 4.25 ppm | |

The compound had a melting point of 169° C. It was subjected to elementary analysis and the following data were obtained:

| | Calculated | Found |
|---|---|---|
| C | 42.5 | 42.6 |
| H | 9.5 | 9.5 |
| P | 18.2 | 18.0 |
| Cl | 20.3 | 20.4 |

EXAMPLE 6:

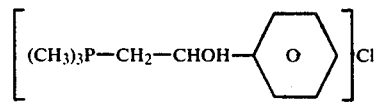

1 mol (76 g) of $(CH_3)_3P$ was reacted with 1 mol (120 g) of styrene oxide at 15° C. in 8 mols of $H_2O$, in the apparatus described in Example 1.

The resulting phosphonium hydroxide solution was neutralized by means of hydrochloric acid and worked up to give $[(CH_3)_3P—CH_2—CHOH—PH]Cl$. It was not possible to obtain the compound in crystalline form; it was obtained in the form of a sirupy mass. 180 g of final product, corresponding to a yield of 77.7%, was obtained.

The compound was identified by NMR-spectroscopy.

| PCH$_3$ | 1.92 ppm | P | −24 ppm |
|---|---|---|---|
| PCH$_2$ | 2.72 ppm | | |
| CH | 5.13 ppm | | |

7.48 ppm 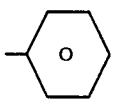

The following data were determined by elementary analysis:

|   | Calculated | Found |
|---|---|---|
| C | 57.2 | 56.8 |
| H | 7.8 | 8.0 |
| P | 13.4 | 13.8 |
| Cl | 14.9 | 14.5 |

EXAMPLE 7: [(CH$_3$)$_2$P(CH$_2$—CHOH—CH$_3$)$_2$]Cl 1 mol (62 g) of (CH$_3$)$_2$PH was reacted with 2 mols (116 g) of propylene oxide at 10° C. in 6 mols of H$_2$O with a pH-value of 12, in the apparatus described in Example 1. The resulting phosphonium hydroxide solution was neutralized by means of hydrochloric acid and worked up to give [(CH$_3$)$_2$P(CH$_2$—CHOH—CH$_3$)$_2$]Cl. It was not possible to obtain the compound in crystalline form; it was obtained in the form of a sirupy mass. 176 g of final product, corresponding to a yield of 82.4%, was obtained.

The compound was identified by NMR-spectroscopy.

| CH$_3$ : 1.34 ppm | P : —27 ppm |
|---|---|
| PCH$_3$ : 1.98 ppm | |
| PCH$_2$ : 2.47 ppm | |
| CH : 4.25 ppm | |

The following data were obtained by elementary analysis:

|   | Calculated | Found |
|---|---|---|
| C | 45.0 | 44.7 |
| H | 9.5 | 9.4 |
| P | 14.5 | 14.7 |
| Cl | 16.1 | 15.9 |

We claim:
1. In the process for making quaternary phosphonium hydroxides of the general formula:

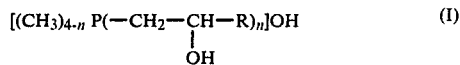

in which R stands either for hydrogen or an aliphatic or aromatic hydrocarbon having 1 to 12 carbon atoms and n stands for 1 or 2, wherein a di- or trimethylphosphine is reacted in an aqueous medium with an epoxide of the general formula:

in which R has the meaning given above, the improvement which comprises: establishing a pH-value of $\geq 12$ in the aqueous medium by means of a base and mixing the starting materials in said medium at $-10°$ to $+35°$ C.

2. The process as claimed in claim 1, wherein the aqueous medium is water or a mixture of water with an organic solvent.

3. The process as claimed in claim 1, wherein 1 to 10 mols of water is used per mol of di- or trimethylphosphine.

4. The process as claimed in claim 3, wherein 3 to 5 mols of water is used per mol of di- or trimethylphosphine.

5. The process as claimed in claim 1, wherein the epoxide is used in excess over the methylphosphine, the excess being based on the stoichiometric quantity necessary to ensure the formation of the particular phosphonium hydroxide to be produced.

6. The process as claimed in claim 1, wherein the pH-value of the aqueous medium is established by means of an alkali metal hydroxide.

* * * * *